US006309837B1

(12) United States Patent
Dean et al.

(10) Patent No.: US 6,309,837 B1
(45) Date of Patent: Oct. 30, 2001

(54) PCR-BASED METHOD FOR IDENTIFYING A FUSARIUM WILT-RESISTANT GENOTYPE IN PLANTS

(75) Inventors: Ralph A. Dean, Apex, NC (US); Yi-Hong Wang, Central, SC (US)

(73) Assignee: Clemson University, Clemson, SC (US)

(*) Notice: Subject to any disclaimer, the term of this patent is extended or adjusted under 35 U.S.C. 154(b) by 0 days.

(21) Appl. No.: 09/417,722

(22) Filed: Oct. 13, 1999

(51) Int. Cl.[7] ....................................................... C12Q 1/68
(52) U.S. Cl. .................................. 435/6; 435/6; 435/91.1; 435/91.2; 435/410; 435/803; 536/254.4; 428/907; 428/99
(58) Field of Search ............................... 435/6, 91.2, 410, 435/803; 536/25.4; 428/907, 99

(56) References Cited

U.S. PATENT DOCUMENTS 6,004,774    12/1999    Marrone et al. .

OTHER PUBLICATIONS

Y.–H. Wang, C.E. Thomas and R.A. Dean; A genetic map of melon based on amplified fragment length polymorphism markers. 8 pages. Received Mar. 12, 1997/Accepted May 20, 1997.
W. P. Wechter, R.A. Dean and C.E. Thomas; Development of Sequence–specific primers that amplify a 1.5–kb DNA marker for race 1 fusarium wilt resistance in Cucumis melo L. 2 pages. HortScience, vol. 33(2), Apr. 1998.
PCT International Search Report, Jan. 8, 2000, 4 pp.

Primary Examiner—W. Gary Jones
Assistant Examiner—Janell E. Taylor
(74) Attorney, Agent, or Firm—Dority & Manning, PA

(57) ABSTRACT

The present invention provides a sensitive assay for objectively determining the genotype of cucurbit plants, particularly species of melon, with respect to resistance or susceptibility to Fusarium wilt infection. The assay of the present invention uses a polymerase chain reaction to amplify sample DNA using either an AM or FM oligonucleotide primer pair. The PCR product which results from either primer pair differs in size, depending upon whether the template DNA was obtained from a plant susceptible or resistant to Fusarium wilt, permitting easy and rapid identification of plant genotype.

18 Claims, 5 Drawing Sheets

5'-CTT CAT CAC TAT TCG AGG ATG AC-3' (SEQ ID : 1; AM-1)

5'-CTT TCT GCA CAC CAA CCA AAA GG-3' (SEQ ID: 2; AM-2)

FIG. 1

5'-GAA GAT GCA AAG AAA AAG AGA AGG-3' (SEQ ID: 3; FM-1)

5'-TCA ATT ATT AAA CAT TCT GAT GCC-3' (SEQ ID: 4; FM-2)

FIG. 2

PCR-BASED METHOD FOR IDENTIFYING A FUSARIUM WILT-RESISTANT GENOTYPE IN PLANTS

FIELD OF THE INVENTION

The present invention is directed toward a method for identifying genetically resistant cucurbit plants using a polymerase chain reaction (PCR) assay. More particularly, the present invention provides a rapid PCR-based method to detect melon plants expressing a Fusarium wilt-resistant genotype.

BACKGROUND OF THE INVENTION

Fusarium wilt is a fungal infection, which is one of the most destructive diseases to affect the production of cucurbit crops. Cucurbits are members of a botanical family, which includes agricultural crops such as melon (muskmelon, honeydew and cantaloupe), watermelon, cucumbers, gourds, pumpkins, squash (summer and winter), and related plants.

Fusarium wilt is a ubiquitous disease. For example, infection with *Fusarium oxysporum* Schlechtend. ex Fr.f.sp. *melonis* Snyder & Hans. occurs throughout North America, Europe and Asia. This forma specialis of *F. oxysporum* infects only melons, but susceptible plants can be infected in all stages of development. The pathogen infects the roots and blocks the uptake of water and nutrients, killing the root and above-ground tissue. In infected fields, yield losses can be as high as 100% (Sherf & MacNab, "Fusarium Wilt of Muskmelon," pgs. 334–337 in VEGETABLE DISEASE AND THEIR CONTROL, 2nd ed., John Wiley & Sons, NY, 1986). Once established in field soil, the pathogen persists indefinitely. Even after prolonged periods of cultivation of non-host crops, the Fusarium wilt pathogen can still be recovered from the soil (Banihashemi & DeZeeuw, The Behavior of *Fusarium Oxysporum* fsp *melonis* in the Presence and Absence of Host Plants, *Phytopathology* 65:1250–1217, 1975). The only economic method for effective disease control is through introgressing the resistant gene into commercial cultivars.

Currently, four races (races 0, 1, 2, and 1,2) of the fungus are defined by their capacity to induce disease in differential melon varieties. The variety Charentais T is susceptible to all races. Doublon, which has the resistance gene Fom-1, is resistant to races 0 and 2. CM17-187, which has the resistance gene Fom-2 is resistant to races 0 and 1. Line MR-1, which has both Fom-1 and Fom-2, is resistant to races 0, 1, and 2. All, however, are susceptible to race 1,2. Race 2 is the most widely distributed in the United States and was the only race known in North America until 1985, when race 1 was discovered in the North Atlantic states (Martyn & Gordon, "Fusarium Wilt of Melon," pgs. 14–15 in Zitter et al., eds., COMPENDIUM OF CUCURBIT DISEASES, APS Press, MN, 1996). Currently, only a few Eastern-type melons are resistant to race 1 (Zuniga et al., Characterization of Pathogenic races of *Fusarium Oxysporum* f.sp. *melonis* causing Fusarium Wilt of Melon in New York, *Plant Dis.* 81:592–596, 1997) and commercial varieties grown in California are susceptible (Gwynn et al., A New Race of *Fusarium oxysporum* f.sp. *melonis* causing Fusarium Wilt of Muskmelon in the Central Valley of California, *Plant Dis.* 81:1095, 1997). Several breeding lines are highly resistant to the disease, including the widely used line MR-1 (Thomas & Jourdain, Role of Host Resistance in Management of Downy Mildew in Muskmelon, pgs. 131–135 in *Proc. Clemson Univ. Cent. IPM Sypm.*, 1989; Thomas et al., Inheritance of Resistance to *Alternana cacumerina* in *Cucumis melo* line MR-1, *Plant Dis.* 74:868–870, 1990; Wang et al., A Genetic Map of Melon (*Cucumis melo* L.) Based on Amplified Fragment Length Polymorphism (AFLP) Markers, *Theor. and Appl. Genet.* 95:791–798, 1997).

Genetic control of resistance to Fusarium wilt has been studied in some detail. Two single dominate genes, Fom-1 and Fom-2, confer resistance to races 0 and 2 and races 0 and 1, respectively. However, resistance to race 1,2 appears to be polygenic (Blancard et al., IN A COLOR ATLAS OF CUCURBIT DISEASES: OBSERVATION, IDENTIFICATION AND CONTROL, John Wiley and Sons, NY, 1994; Zink & Thomas, Genetics of Resistance to *Fusarium oxysporum* f.sp. *melonis* races 0, 1, and 2 in Muskmelon Line MR-1, *Phytopathology* 80:1230–1232, 1990).

Traditionally, artificial inoculation techniques were used to evaluate Fusarium wilt resistance in melon breeding programs. However, this method is very time consuming. Young seedlings must be uprooted; roots pruned and dipped into an inoculum of appropriate spore concentration; seedlings replanted; and symptom development monitored constantly over four weeks or longer (Wechter et al., Development of Sequence Specific Primers which Amplify a 15 kb DNA Marker for Race 1 Fusarium Wilt Resistance in Cucumis melo, Hortscience 33:291–292, 1998; Zink & Thomas, Genetics of Resistance to *Fusarium oxysporum* f.sp. *melonis* races 0, 1, and 2 in Muskmelon Line MR-1, *Phytopathology* 80:1230–1232, 1990). Furthermore, using the traditional method of artificial inoculation, there are occasional escapes, even when plants are evaluated under a controlled environment; i.e., susceptible plants which survive the inoculation procedure, resulting in a mis-scoring of the phenotype.

Therefore, in view of the deficiencies of prior art methods, a rapid method which reliably identifies Fusarium resistant melon genotypes, would be highly desirable. The method of the present invention provides a reliable and rapid assay to identify race 1 Fusarium resistance in cucurbits, especially melons. This novel method uses unique DNA primers in a rapid assay using the polymerase chain reaction (PCR).

PCR is a technique by which a small fragment of deoxyribonucleic acid (DNA) can be rapidly duplicated, or cloned, to produce multiple DNA copies. The strength of the PCR technique is that it can be used to identify genetically resistant plants from minute amounts of tissue samples because it proceeds in a series of cycles, with each successive round doubling the amount of DNA present in the sample. Thus, more than one billion copies of a single DNA fragment can be made in just a few hours, by mimicking the natural DNA replication process that occurs in living cells.

There are three phases essentially in a PCR reaction. In the first phase, denaturation, the original DNA extracted from the sample is heated to a temperature of from about 90° C. to 95° C. for a brief period, causing the two strands of DNA to separate. In the second or annealing phase, the temperature of the sample tube is lowered over a short period of time, allowing for the added oligonucleotide primers to bind to the separated DNA strands in a complementary fashion. In the final polymerization phase the temperature of the sample mixture is again raised, to approximately 72° C., allowing the polymerase enzyme to copy the segments of DNA located between annealed primer pairs rapidly. The three phases make up one complete PCR cycle, and take less than five minutes to complete.

The PCR reaction is repeated for a specified number of cycles, usually between 25 and 35, allowing the entire procedure to be completed in three to four hours. As an added advantage, this procedure can be automated with the use of commercially available thermal cyclers, allowing the entire procedure to be conducted using pre-determined parameters.

Following the completion of the PCR procedure, the samples may be run out on an electrophoresis gel to verify the presence of the desired DNA fragment. The electrophoresed products may be visualized using an ethidium bromide dye, or may be positively identified by hybridization with a probe specific for the fragments of interest.

Over the past several years PCR technology has been shown to be applicable to the diagnosis of many human, animal, and plant organisms, and a variety of clinical assays have been evaluated. Results suggest that PCR is highly sensitive and, by varying conditions used, the technique can accurately discriminate between even closely related species. However, PCR technology has never been used to identify melon cultivars having resistance to Fusarium wilt, as in the present invention, because markers linked to resistance genes have not been known. Nor have the primers and conditions suitable for identifying genetically resistant melon cultivars been known.

By identifying markers linked to Fom-2 in melon, and developing specific PCR primers from these markers, PCR technology can be used to provide an objective assay to identify melon cultivars exhibiting resistance to Fusarium wilt. Further, it is believed that the PCR assay of the present invention is applicable for identifying other cucurbit crops that exhibit Fom-2-based resistance to Fusarium wilt. Thus, the present invention allows for the rapid identification of melon plants and other cucurbits containing genotypic resistance to the race 1 Fusarium wilt pathogens and requires only small amounts of plant tissue DNA to provide a result. By providing a rapid, non-destructive assay to detect Fusarium resistant genotypes in cucurbits, the PCR assay of the present invention is useful in the marker-assisted breeding programs presently used by most seed and agricultural companies.

SUMMARY OF THE INVENTION

The present invention recognizes and addresses the foregoing disadvantages and others of prior art constructions and methods. Accordingly, it is an object of the present invention to provide an assay for identifying plant genotypes resistant to Fusarium wilt.

Another object of the present invention is to provide a method for identifying a genotype exhibiting Fusarium wilt resistance that is highly sensitive and rapid.

Yet another object of the present invention is to provide specific oligonucleotide primers which can be used to identify cultivars resistant to race 1 Fusarium wilt.

Still another object of the present invention is to provide a rapid PCR assay using specific oligonucleotide primers to identify melon cultivars genetically resistant to *Fusarium oxysporum* f.sp. *melonis* infection.

These and other objects of the present invention are achieved by providing specific oligonucleotide primers for use in a PCR based assay to identify Fusarium wilt resistant cucurbits, such as melon plants. Specifically, the PCR assay of the present invention is useful in marker-assisted breeding programs to identify host plants containing resistance to the Fusarium wilt pathogen *Fusarium oxysporim* f.sp. *melonis* race 1.

The identification method of the present invention uses a PCR technique, whereby DNA is extracted from plant cells of interest and is then replicated a number of times such that the original amount of DNA present is amplified greatly. The identification assay requires the addition of unique primers specific for DNA segments closely associated with Fom-2, known to confer Fusarium wilt resistance in melon plants, and results in enhanced amplification of a PCR product. The PCR product can be putatively identified by visualization or definitively identified by hybridization with a specific probe.

The PCR process is initiated by isolating genomic DNA from cucurbit plants of interest to serve as a template during the PCR amplification. Specific oligonucleotide primers are allowed to hybridize, or bind, to areas which are complementary in the target DNA. The primers then serve as sites to allow the polymerase enzyme to fill in the area between the bound primers, resulting in a doubling of the DNA. By repeating this cycle many times, a billion or more copies of the original DNA can be made. Specificity of the amplification procedure is controlled by the uniqueness of the primers, and the conditions of the PCR reaction.

Following PCR amplification, PCR products are electrophoresed into agarose gels, along with a DNA ladder for determining the size of the PCR product. The PCR product can be putatively identified using visual comparison to a size marker, or can be definitively identified by means of hybridization with a specific probe.

The PCR assay of the present invention provides a method for the early identification of cucurbit genotypes resistant to the Fusarium wilt pathogen *Fusarium oxysporum* f.sp. *melonis* race 1. Because PCR technology can amplify very small quantities of plant DNA, the method of the present invention allows for rapid, non-destructive identification of Fusarium wilt resistant genotypes in melons and other host plants, thereby providing a method amenable to high through-put analysis. Such early identification assists plant breeders and other employees of commercial agricultural companies to identify Fusarium wilt resistant plants for use in breeding protocols.

As discussed above, the only economically feasible measure to control Fusarium wilt in melon production is the use of resistant varieties of plants. Traditionally, artificial inoculation has been used to evaluate Fusarium wilt resistance in breeding programs. However, artificial inoculation is time consuming, expensive and may be prone to error. For example, some plants may escape infection, while others may die from root damage. In contrast to the artificial inoculation method, the method of the present invention is more rapid, and may be a more sensitive way to identify plants carrying genetic resistance to Fusarium wilt.

The present method is also more cost effective when compared with currently used methods. Artificial inoculation requires large amounts of potting media, as well as a high degree of skill to uproot seedlings, artificially inoculate the seedlings with the appropriate spore concentration, replant the inoculated seedlings, and monitor symptom development. In contrast, the identification method of the present invention permits the simultaneous amplification of multiple samples and can be accomplished using very small amounts of plant DNA, on the order of 50 nanograms (ng) or less.

Broadly speaking, the identification method of the present invention involves extracting genomic DNA from cells found in plant tissue, such as stems and leaves, or seed; replicating the DNA template with the use of specific oligonucleotide primers; amplifying the complementary DNA for between approximately thirty to approximately forty cycles of thermal cycling; and producing a PCR product which can be identified based on size or on hybridization ability with an oligonucleotide probe specific for the desired PCR product.

In summary, the method of the present invention is useful for identifying cucurbit genotypes, especially those of melon, exhibiting resistance to the Fusarium wilt pathogen *Fusarium oxysporum*, especially *F. oxysporum* f.sp. *melonis* race 1. A PCR assay performed according to the present invention greatly increases the ease with which plant breeders detect Fusarium wilt resistant plants for use in cucurbit breeding protocols.

BRIEF DESCRIPTIONS OF THE FIGURES

A full and enabling disclosure of the present invention, including the best mode thereof, to one of ordinary skill in the art, is set forth more particularly in the remainder of the specification, including reference to the accompanying figures, wherein:

FIG. 1 is the nucleotide sequence for the AM primer set.

FIG. 2 is the nucleotide sequence for the FM primer set.

DETAILED DESCRIPTION OF PREFERRED EMBODIMENT

Figure 3:
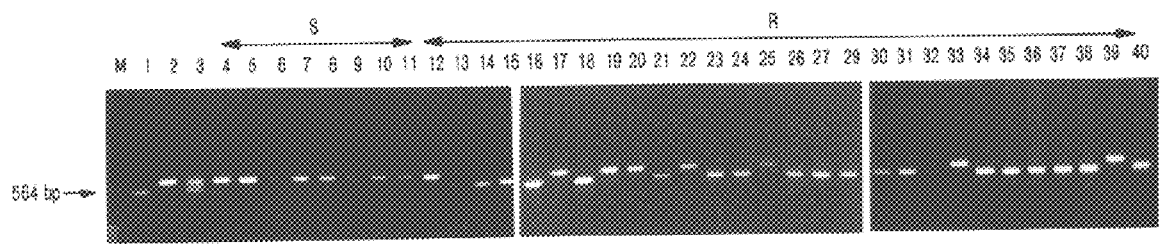
FIG. 3 is a photograph of the agarose gel results using the FM primers in the PCR assay of the present invention to identify Fusarium-resistant and Fusarium-susceptible melon genotypes.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present inventions which broader aspects are embodied in the exemplary construction.

The identification method of the present invention uses the polymerase chain reaction (PCR) technique, whereby total genomic DNA is extracted from plant tissues, cells, and seed, and is then amplified using specific oligonucleotide primers to target desired DNA regions for replication and amplification. If the DNA sequence complimentary to the oligonucleotide primers is found in the samples to be analyzed, a PCR product will be generated that can be visualized using non-specific (e.g., ethidium bromide staining) or specific detection methods (e.g., definitive diagnosis of PCR products by probing the PCR product with specific oligonucleotide probes).

The present identification method involves isolating genomic DNA from cells of plant leaves, stems, or seed, using techniques well known to those skilled in the art. Standard molecular biology textbooks, such as MOLECULAR CLONING: A LABORATORY MANUAL, 2nd ed., (Sambrook et al., Cold Spring Harbor Laboratory Press, Cold Spring Harbor, N.Y., 1989) and METHODS FOR GENERAL AND MOLECULAR BACTERIOLOGY (eds., Philipp Gerhardt et al., American Society for Microbiology, Washington, DC, 1994) may be consulted for procedures to isolate DNA, without undue experimentation by those of ordinary skill in the art.

Following isolation of genomic DNA from plant tissue of interest, the sample DNA is denatured such that the doubled strand of DNA is separated into individual strands. Each strand is then replicated, using a pair of specific oligonucleotide primers that give rise to a PCR product of particular size. For example, one primer set, designated FM primer pair, gives rise to a PCR product of approximately 555 base pair (bp) in resistant plants and 596 bp in susceptible plants. Another primer set, designated the AM primer pair, yields a product of approximately 1.682 kilobases (kb) in resistant plants and 1.783 kb in susceptible plants.

In one embodiment of the present invention, sample DNA is amplified using the PCR technique for about thirty to about forty cycles; after which the resulting PCR product is electrophoresed onto agarose gels for verification. In one embodiment, the PCR product is visualized by incorporating ethidium bromide, a dye which exhibits strong affinity for DNA, into the agarose gel. The PCR product is then visualized under ultraviolet light and its size estimated by comparison with a known standard, like a lambda DNA marker.

In another embodiment, sample DNA is amplified using modified PCR primers. Modification of the primers includes the addition of a biotin moiety to the 5' end of the forward primer and the addition of a fluorescein moiety to the 5' end of the reverse primer. Amplification of the genomic DNA is performed for approximately thirty to approximately forty cycles, before visualization of the PCR product is performed using a colorimetric method. For visualization, the amplified DNA is first attached to the wells of a microtiter plate coated with avidin (NEUTRAVIDIN), which binds the DNA chemically via the biotin moiety. After washing off excess or unbound PCR product, an enzyme is attached to the DNA via the fluorescein moiety. Excess or unbound enzyme is washed away prior to the addition of a color substrate. The enzyme reacts with the substrate forming a colored product. The intensity of the color can be measured using commercially available readers (ELISA readers), thus permitting the rapid processing of multiple samples.

Specifically, the diagnostic method of the present invention includes the following steps: (a) removing a sample of leaf, stem, or seed from the plant to be tested for race 1 genetic resistance to the Fusarium wilt pathogen; (b) extracting the DNA from the cells of the sample to use as a template in the assay of the present invention; (c) replicating the desired region in the DNA template by binding specific oligonucleotide primers in a complementary fashion—such primers designed to give rise to a PCR product having a size different from the size of a product produced from amplifying any undesired genomic DNA; (d) amplifying complimentary DNA by conducting the polymerase chain reaction for about thirty to about forty cycles; and (e) identifying the PCR product by agarose gel or ELISA visualization or probe hybridization to determine whether a sequence coding for a race 1 Fusarium wilt-resistant genotype is present.

The present invention may be better understood with reference to the following examples:

EXAMPLE 1
Genomic DNA Isolation Procedure

DNA was isolated from the leaves of melon plants using the cetyltrimethylammonium bromide (CTAB) method modified from Lichtenstein and Draper ("Genetic Engineering of Plants," pgs. 67–119 in D. M. Glover, ed., DNA CLONING: A PRACTICAL APPROACH, Vol. II, IRL Press, London, 1985) and Baudraco-Amas (A Simple and Inexpensive Method for DNA Extraction from *Cucumis melo* L., *Cucurbit Genet. Coop. Rep.* 18: 50–51, 1995), as follows:

About one-tenth gram (0.1 g) to about one gram (1.0 g) of leaves obtained from melon seedlings was ground in liquid nitrogen to a fine powder and transferred to 20 ml extraction buffer (10 mM EDTA; 50 mM Tris-HCl, pH 8.0; 0.7 mM NaCl; 1% or 4% CTAB; and 1% β-mercaptoethanol) in 50 ml tubes. The mixture was incubated at 65° C. for 30 min with occasional agitation, cooled to room temperature (RT), mixed with an equal volume of 24 chloroform: 1 octanol (v/v), and centrifuged for 20 min at RT at 5000 rpm using a Sorvall HS-4 rotor. The aqueous phase was transferred to a new tube and 2 ml of CTAB:nAcL (10% CTAB in 0.7 M NaCl) added before an equal volume of chloroform:octanol was added, as above. The mixture was again centrifuged as above. The aqueous phase was transferred and an equal volume of precipitation buffer (10 mM EDTA; 50 mM Tris-HCl; and 1% CTAB) was added. The mixture was incubated for 30 min at 65° C. and centrifuged as above. Precipitate was dissolved in 200–500 μl of 1M NaCl. RNAase was added to a concentration of 100 ng/μl, the mixture incubated for 20 min at 37° C., and the DNA was phenol/chloroform extracted and precipitated with 2 volumes of ethanol. The DNA was dissolved in $H_2O$ to a final concentration of 40–50 ng/μl.

EXAMPLE 2

Identification of AM and FM Primers Pairs

Amplified Fragment Length Polymorphism (AFLPs) and Random Amplified Polymorphic DNA (RAPDs) were used to identify dominant markers closely linked to Fom-2, using bulked segregant analysis (Michelmore et al, Identification of Markers to Disease-Resistance Genes by Bulked Segregant Analysis: A Rapid Method to Detect Markers in Specific Genomic Regions By Using Segregating Populations, *PNAS USA* 88: 9828–9832, 1991) on DNA from a previously constructed $F_2$ population. The $F_2$ population resulted from a cross between MR-1 and AY (Ananas Yokneum) parental lines. MR-1 is a Fusarium resistant line, while the AY line is susceptible to Fusarium wilt. The AFLPs and RAPDs were mapped in a separate backcross population, and the most tightly linked markers converted to a codominant form.

DNA Marker Analysis: AFLP analysis was performed as described previously (Vos et al., AFLP: A New Technique for DNA Fingerprinting, *Nucl. Acid Res.* 23: 4407–4414, 1995; Wang et al., A Genetic Map of Melon [*Cucumis melo* L.] based on Amplified Fragment Length Polymorphism [AFLP] Markers, *Theor. Appl. Genet.*, 95: 791–798, 1997; the contents of which are incorporated herein in their entirety), using EcoR I/Mse I primer pairs (Life Technologies, Gaithersburg, Md.) and Pst I/Mse I adapter sequences from Thomas et al. (Identification of Amplified Restriction Fragment Polymorphism (AFLP) Markers Tightly Linked to the Tomato Cf-9 Gene for Resistance to *Cladosporium fulvum*, *Plant J.* 8: 785–794, 1995). Primers were either synthesized by Operon Technologies (Alameda, Calif.), IDT (Coralville, Iowa) or obtained from Life Technologies (Gaithersburg, Md.). The AFLP primers (adapter with selective nucleotides) used are as follows:

| Restriction Enzymes Used | Primers with +2 or +3 selective nucleotides | |
|---|---|---|
| Pst I (Pharmacia, Piscataway, NJ) | P—AC, —AG, —CC, —CG, —CA, —CT, —GG, —GA, —GC, —GT | |
| EcoRI (Life Technologies, Gaithersburg, MD or Promega, Madison, WI) | Set I: | E—TA, —TG, —TT, —AT, —TC, |
| | Set II: | E—AAC, —AAG, —ACA, —ACT, —ACC, —ACG, —AGC, —AGG, —AGA, —AGT, —ATC, —ATG |
| Mse I (New England Biolabs Beverly, MA). | Set I: | M—CGA, —CCG, —CGC, —CCA, —CGG, —CGT, —CCT, —CCC, |
| | Set II: | M—CTG, —CAA, —CTT, —CAC, —CAG, —CTC, —CAT, —CTA, |
| | Set III: | M—GGT, —GCT, —GCG, —GGC, —GGA, —GCC, —GCA, —GGG, |
| | Set IV: | M—CC, CG |

Two Hundred forty Pst I/Mse I primer pairs were used, including 10 Pst I primers with two selective nucleotides and 24 Mse I primers (Sets 1, II, III) with three selective nucleotides. For EcoR I/Mse I primers, 200 primer combinations were tried, including the 57 primer pairs previously tested (Wang et al., 1997).

RAPD marker analysis was modified from Wechter et al. (Development of Sequence Specific Primers which Amplify a 1.5 kb DNA Marker for Race 1 Fusarium Wilt Resistance in *Cucumis melo*, *HortScience* 33: 291–292, 1998). 320 oligo-10 mers were examined using thermocycling and components previously described for RAPD analysis (Wang et al., 1997). AFLP and RAPD analysis were initially tested using bulked segregant analysis. Homozygous resistant (RR) and susceptible (SS) bulk DNA pools targeted in the Fom-2 region were constructed previously from the $F_2$ population (Wechter et al, 1995). The RR bulk was prepared from 7, and the SS bulk from 11, $F_2$ plants respectively. Bulked segregant analysis was performed as described by Michelmore et al. (1991).

Bands were scored visually. Primers (RAPD) and primer pairs (AFLP) that yielded bands potentially linked to Fom-2 based on analysis of the bulks were tested against the 60 individual backcross progenies segregating for this gene. Linkage analysis was performed as described by Wang et al. (1997) using MapMaker 2.0 for Macintosh. Development of Codominant Markers from Markers Closely Linked to Fom-2: To convert a dominant marker to codominant, a restriction fragment length polymorphism (RFLP) was identified using the respective marker as a hybridization probe. Probes were prepared as follows. The 1.5 kb 596-1 band amplified by sequence specific primers (Wechter et al., Development of Sequence Specific Primers which Amplify a 1.5 kb DNA Marker for race 1 Fusarium Wilt Resistance in *Cucumis*

*melo. HortScience* 33: 291–292, 1998) from the MR-1 species of melon was purified from an agarose gel using a GeneClean Kit (Bio101, CA) and used directly in the radiolabeling step. For AFLP markers, bands were cut out of dried AFLP sequencing gels using the autoradiogram as a guide and boiled in water for 15 min. After centrifugation, DNA was precipitated with 0.1 vol 3M sodium acetate and 3 vol of ethanol. Precipitated samples were resuspended in 10 μl of water after washing with 70% ethanol and 4 μl of each sample was used for reamplification. The reamplified products were run on 1% agarose gels, bands were cut out, frozen at −80° C. for 30 min and immediately centrifuged for 12 min at 16,000 g and liquid transferred to a new centrifuge tube. The reamplified AFLP fragment from AGG/CCC was cloned into the pGEM-T vector (Promega, Wis.). The 596-1 fragment had been cloned previously (Mechter et al., 1998). These fragments were radiolabelled with $\alpha$-$^{32}$P dCTP using a random labeling approach (Amersham, Ill.), and used to probe genomic blots of melon digested with six restriction enzymes (Bam HI, Bgl II, Eco RI, Eco RV, Hind III and Xba I) from MR-1 and AY. To clone the genomic DNA fragments identified by Southern hybridization, MR-1 and AY were digested with the appropriate enzyme and separated on a preparative agarose gel. A subgenomic library was constructed from each region containing the target fragment. Each library was screened by colony hybridization using the appropriate probe and candidate clones identified. At least two clones were sequenced using Big-Dye on an ABI 377 sequencer (PE Biosystems, CA). Sequences from both parents were compared using GeneWorks 2.3 (IntelliGenetics, CA). Primers were designed and custom synthesized by IDT (Coralville, Iowa).

DNA Sequencing: Fifty to two hundred ng templates were used for most sequencing reactions. For each reaction in 10 μl volume, 1 μl BigDye mix, 1 μl primer (0.8 μM), 3 μl buffer (200 mM Tris-HCl, pH 9.0, and 5 mM $MgCl_2$) were added. The cycle sequencing reaction was run for 30 cycles at 96° C./30 s, 50° C./15 s and 60° C./4 min. After cycle sequencing reactions, 0.1 volume 3 M sodium acetate and 2 volumes of ethanol were added and incubated on ice for 20 min. Cycle sequencing products were precipitated by centrifugation at 4° C. for 20 min and washed with 70% ethanol. After drying, 2 μl loading buffer (83% formamide, 25 mM EDTA and BlueDextran 50 mg/ml) was added. A 5% polyacrylamide gel was prepared, and the gel was run at a constant voltage of 3000 v for 3.5 hrs in an ABI 377. Lane tracking was done on a Macintosh computer and analyzed using GeneWorks 2.3.

Results: To identify AFLP markers linked to Fom-2, bulked segregant analysis was performed on a previously constructed $F_2$ population that was segregating for resistance to Fusarium wilt race 1. Homozygous resistant (RR) and susceptible (SS) bulked DNA samples were first screened using AFLPs with all 240 combinations of Pst I/Mse I primer pairs. Most primer pairs generated 30–70 bands on a sequencing gel. However, no reliable polymorphic bands were detected between the RR and SS bulks, although numerous polymorphisms were detected between the parents MR-1 and AY. For EcoR I/Mse I primers, 200 primer combinations were tried, including the 57 primer pairs previously tested in an earlier mapping study. Fifteen candidate bands were identified that were present only in the RR bulk. As expected, these bands were present in the resistant parent MR-1, but absent in AY. Finally, 320 RAPD primers additional to those used previously (Wechter et al., 1995) were screened against the bulks. Eighty-nine of these primers detected polymorphism between MR-1 and AY, but only 596-1, a RAPD marker previously found to be linked to Fom-2 (Wechter et al., 1995), identified polymorphism between the bulks.

The AFLP markers identified by bulked segregant analysis together with 596-1 were used to screen individuals from the F2 population used to construct the bulks. These markers were used to screen a separate, larger population of 60 BC individuals constructed by Wang et al. (1997) which also segregates for Fom-2. The markers were scored and ordered using a LOD score of 6.0 and recombination fraction of 0.25.

The RAPD marker 596-1 was mapped using the sequence specific primers (596-1s) derived from the polymorphic band (Wechter et al. 1998) and was found to cosegregate perfectly with Fom-2 in the 60 BC progeny. Previously this marker was found to be very tightly linked to Fom-2 with two recombinants in 96 F2 progeny evaluated (Wechter et al. 1995). The newly identified AFLP marker AGG/CCC also cosegregated perfectly with Fom-2 in the backcross. AFLP marker ACT/CAT1, which had been previously localized on the map of Wang et al. (1997), revealed a single recombinant with Fom-2.

Development of Codominant Markers: The two markers (AGG/CCC and 596-1 s) that cosegregated with Fom-2 in the backcross were converted to codominant PCR markers. In each case, the marker DNA fragment was used as a probe to reveal RFLP polymorphisms in genomic blots of parental DNA, and polymorphic RFLP bands were subcloned and sequenced. In genomic DNA blots, $^{32}$p labeled 596-1s hybridized to two Xba I fragments in MR-1 (3.5 kb and 600 bp) and to two Xba I fragments in AY (2.5 and 2.2 kb). Since the RAPD band produced from MR-1 had been sequenced previously (GenBank Accession Number: AF005262), only AY fragments were cloned here. Sequence comparison between the aligned regions in MR-1 and AY revealed that MR-1 contained a number of small deletions (primarily poly-T) compared with AY. The AY sequence has been deposited in GenBank (Accession Number: AF151365).

The AGG/CCC AFLP band also identified a polymorphism in Xba I digestions of the parental DNA: a single fragment in MR-1 (2.4 kb) and AY (2.55 kb). After clones were recovered from subgenomic libraries, the ends of the clones were sequenced and found to be identical between MR-1 and AY. This suggested that the polymorphic sequence(s) indicated by the RFLP lay in the inner region.

The original AFLP AGG/CCC fragment from MR-1 was also cloned and sequenced and compared to the corresponding sequence from AY. Both sequences were 195 bp in length, but the Mse I site in AY was changed so that the fragment could not be amplified in AY using the AFLP primers. The sequence at the EcoR I end was the same for both MR-1 and AY. In total, there were five base changes between the two 195 bp sequences.

For each marker, PCR primer pairs were designed from sequences common to both MR-1 and AY. The codominant markers developed from 596-1 and AGG/CCC were named FM and AM, respectively. When used to screen the BC progeny, the converted markers FM and AM were found to cosegregate perfectly with Fom-2, as expected.

FIG. 1 depicts the nucleotide sequence of the AM primer pair (SEQ ID:1 corresponds to the forward primer and SEQ ID:2 corresponds to the reverse primer), while the sequence of the FM primer set is depicted in FIG. 2 (SEQ ID:3 corresponds to the forward primer and SEQ ID:4 corresponds to the reverse primer).

EXAMPLE 3
PCR Identification of Fusarium-Resistant and Fusarium-Susceptible Melon Genotypes Using the PCR identification assay of the present invention, 45 melon genotypes from major production regions around the world were analyzed, to determine whether the correlation between AM and FM fragment sizes and race 1 resistance extends beyond the parental lines MR-1 and AY.

DNA was extracted from the leaves of Fusarium-resistant and susceptible melon plants, as described in Example 1. The PCR reaction mixture contained in the range of 5–20 ng of melon DNA, 0.8 µl of 20X PCR reaction buffer (available commercially from Epicenter, Madison, Wis.), 2.5 mM $MgCl_2$, 0.8 mM deoxynucleotide triphosphates, 1.0 µM primer, and 0.2 units of Tfl DNA polymerase (Epicenter, Madison, Wis.) in a total volume of 20 µl. All tubes were overlaid with one drop of mineral oil, and PCR amplification was performed in a MJ Research Thermal Cycler (Model 210, Watertown, Mass.) using the following profile: Reaction conditions were initial denaturation at 94° C. for 5 min, followed by between 35 amplification cycles of denaturation at 94° C. for 1 min, annealing at 51° C. for 1 min and extension at 72° C. for 2 min. A final extension at 72° C. for 5 min was done before holding samples at 4° C. until use.

The entire 20 µl sample volume was loaded onto a 1% agarose gel for electrophoresis at 5 V/cm with 1X TAE buffer (containing 40 mM Tris and 1 mM EDTA). Products were visualized by staining gels with 0.4 µg/ml ethidium bromide. Amplification of DNA from a resistant genotype, using the AM pair as the primer set, yielded a product of approximately 1.682 kb. In contrast, the AM primer pair produced a fragment of approximately 1.783 kb, when DNA from a susceptible genotype was used as a template. The FM primer pair yielded a product of approximately 555 bp, when amplifying DNA from a Fusarium-resistant genotype, while a 596 bp product resulted when DNA from genetically susceptible plants was used as a template.

The following table, listing the geographical origin and known genotype of the 45 melon samples tested, summarizes the PCR testing results, as follows:

Table 1. PCR Identification of Resistant and Susceptible Genotypes

| Genotype | R/S | Origin | FM | AM |
|---|---|---|---|---|
| 1. MR-1 | R | India | + | + |
| 2. AY | S | Israel | − | − |
| 3. F1 | R | MR-1xAY | + | + |
| 4. Perlita | S | USA | − | − |
| 5. PI 124112 | S | India | − | − |
| 6. Sweet Supreme | S | USA | − | − |
| 7. Supermarket | S | USA | − | − |
| 8. Hymark | S | USA | − | − |
| 9. Dorado | S | USA | − | − |
| 10. Topmark | S | USA | − | − |
| 11. PMR-45 | S | USA | − | − |
| 12. Persia 202 | R | Iran | −** | −** |
| 13. Freeman's Cucumber | R | Japan | + | + |
| 14. CM 17-187 | R | Far East | + | + |
| 15. PI 164723 | R | India | + | + |
| 16. Charentais Fom-2 | R | France | + | + |
| 17. PI 125915 | R | Afghanistan | −** | + |
| 18. Perlicha 1.5 | R | Guadeloupe | + | + |
| 19. Ouzbeque I | R | USSR | −** | + |
| 20. Samar Cande | R | USSR | −** | + |
| 21. Opera | R | USA | + | + |
| 22. Meshed | R | Iran | −** | + |
| 23. Isabelle | R | France | + | + |
| 24. Nanbukin | R | China | + | + |
| 25. LJ 34340 | R | Far East | −** | −** |
| 26. Ginsen Makuwa | R | Japan | + | + |
| 27. LJ 90389 | R | Far East | + | + |
| 28. Chenggam | R | Korea | + | + |
| 29. LJ 90279 | R | Far East | + | + |
| 30. Kanro Makuwa | R | Japan | + | + |
| 31. Shiroubi Okayama | R | Japan | + | + |
| 32. Aodaisimouri | R | Japan | + | + |
| 33. Sisi | R | Iran | −** | −** |
| 34. Tokio Mammuth | R | Japan | + | + |
| 35. Ogon 9 | R | Japan | + | + |
| 36. K 2005 | R | China | + | + |
| 37. Kogane Sennari Makuwa | R | Japan | + | + |
| 38. Showa Kogane Nashi Makuwa | R | Japan | + | + |
| 39. PI 157084 | R | China | −** | −** |
| 40. Nyumelon | R | Japan | + | + |
| 41. Durango | S | USA | − | − |
| 42. Alaska | S | USA | − | − |
| 43. Harper Hybrid | S | USA | − | − |
| 44. Roadside | S | USA | − | − |
| 45. Earli-Dew | S | USA | − | − |
| Total Incorrect | | | 8 | 4 |

Genotypes with known Fom-2 phenotypes: R = resistant; S = susceptible.
"+" - marker band associated with resistant parent MR-1 in a genotype is present,
"−" = marker band associated with susceptible parent AY is present;
** = disagreement between marker and disease phenotype.

Figure 4:
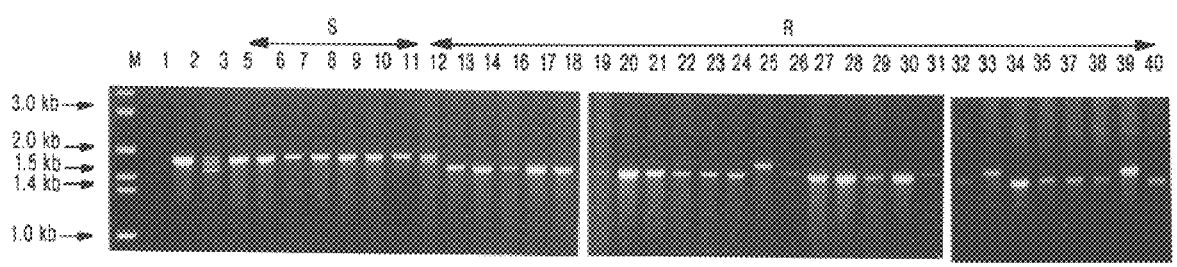
FIG. 4 is a photograph of the agarose gel results using the AM primers in the PCR assay of the present invention to identify Fusarium-resistant and Fusarium-susceptible melon genotypes.

FIGS. 3 and 4 are photographs of agarose gel results from the experiments outlined above. The gels in these photographs show the PCR products resulting from amplification of the various melon isolates using the AM primers and FM primers respectively. Lanes designated as "S" indicate that the PCR product amplified in the PCR assay of the present invention corresponds to a race 1 Fusarium wilt-susceptible genotype. In contrast, lanes identified as "R" indicate that the resulting PCR product corresponds to a race 1 Fusarium wilt-resistant genotype.

The gel in FIG. 3 was loaded so that the gel lane numbers correspond to the sample numbers in Table 1. Thus, samples loaded onto the gel are as follows:

M: lambda DNA marker; 1: MR-1; 2: AY; 3:F1; 4: Perlita; 5: PI 124112; 6: Sweet Supreme; 7: Supermarket; 8: Hymark; 9: Dorado; 10: Topmark; 11: PMR45; 12: Persia 202; 13: Freeman's Cucumber; 14: CM 17–187; 15: PI 164723; 16: Charentais Fom-2; 17: PI 125915; 18: Perlicha 1.5; 19: Ouzbeque I; 20: Samar Cande; 21: Opera; 22: Meshed; 23: Isabelle; 24: Nanbukin; 25: LJ 34340; 26: Ginsen Makuwa; 27: LJ 90389; 29: LJ 90279; 30: Kanro Makuwa; 31: Shiroubi Okayama; 32: Aodaisimouri; 33: Sisi; 34: Tokio Mammuth; 35: Ogon 9; 36: K 2005; 37: Kogane Sennari Makuwa; 38: Showa Kogane Nashi Makuwa; 39: PI 157084; 40: Nyumelon.

The gel in FIG. 4 was loaded in a similar fashion to the gel in FIG. 3.

The samples in the lanes are as follows:

M: lambda DNA marker; 1: MR-1; 2: AY; 3:F1; 5: PI 124112; 6: Sweet Supreme; 7: Supermarket; 8: Hymark; 9: Dorado; 10: Topmark; 11: PMR-45; 12: Persia 202; 13: Freeman's Cucumber; 14: CM 17–187; 16: Charentais Fom-2; 17: PI 125915; 18: Perlicha 1.5; 19: Ouzbeque I; 20: Samar Cande; 21: Opera; 22: Meshed; 23: Isabelle; 24: Nanbukin; 25: LJ 34340; 26: Ginsen Makuwa; 27: LJ 90389; 28: Chenggam; 29: LJ 90279; 30: Kanro Makuwa; 31: Shiroubi Okayama; 32: Aodaisimouri; 33: Sisi; 34: Tokio Mammuth; 35: Ogon 9; 37: Kogane Sennari Makuwa; 38: Showa Kogane Nashi Makuwa; 39: PI 157084; 40: Nyumelon.

As shown in FIG. 3 and Table 1, amplifying DNA with the AM primers in the PCR assay of the present invention identified the samples in lanes 4–11 as susceptible, while the samples in lanes 12–40 were identified as resistant to race 1 Fusarium wilt. In FIG. 4, results of the PCR assay using the FM pair as primers identified the samples in lanes 5–11 as possessing a susceptible genotype, while lanes 12–40 were identified as resistant.

Use of the AM primers, in the PCR assay of the present invention, resulted in the correct identification of 41 of the 45 samples, while the FM primers correctly identified the susceptible or resistant genotype in 37 of the 45 samples tested.

As is shown in Table 1, all of the mismatches involved generating the susceptible-associated band in resistant genotypes. The four phenotypes misidentified, when the AM primers were used in the assay (Persia 202, LJ 34340, Sisi and PI 157084), were also misidentified when the PCR assay was performed using the FM primers. Because all four of these misidentified samples originated from Asia (i.e., Iran and the Far East), it is possible that the segment of the genome corresponding to the bands predicting resistance may have been lost during intense selection for resistance. Alternatively, the source of resistance in these genotypes may differ from that in the other samples. Lastly, it is also possible that these four lines were not completely homozygous.

EXAMPLE 4
PCR Amplification of Cucumber DNA

The PCR assay of the present invention successfully amplified DNA from cucurbits other than melon, when the FM pair was used as the primer set.

Figure 5:
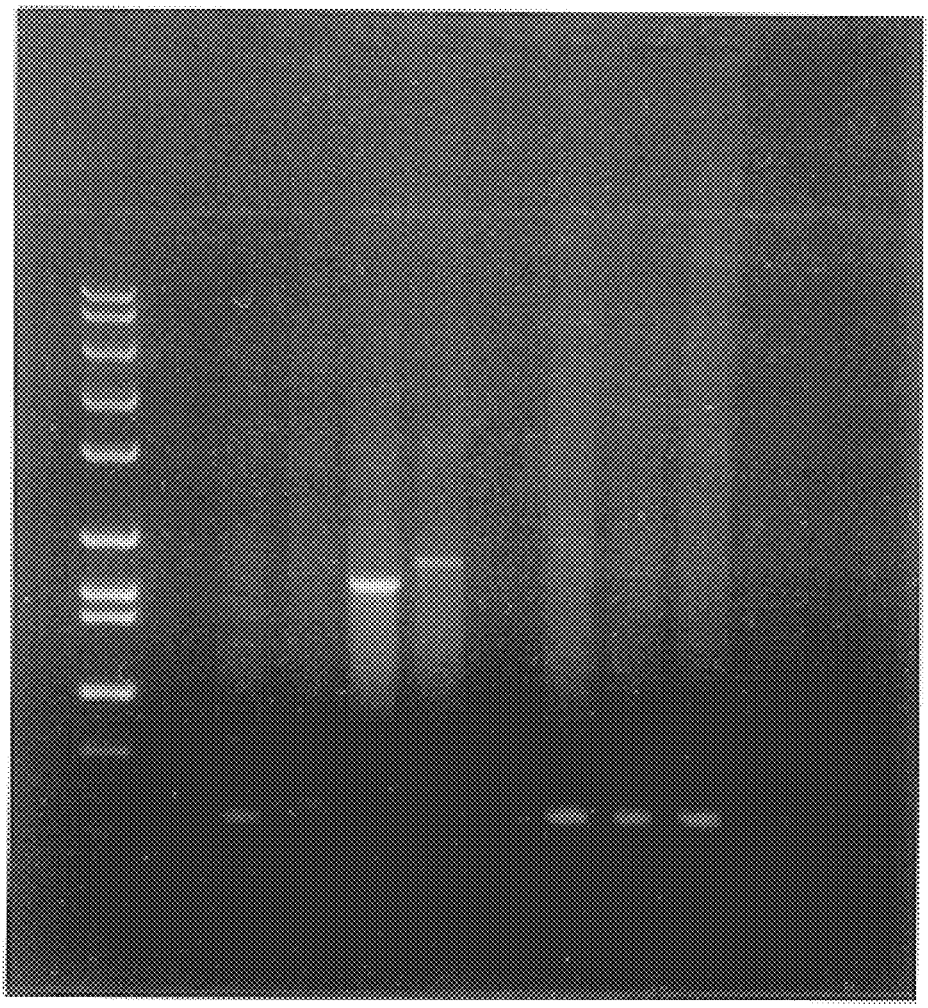
FIG. 5 is a photograph of the agarose gel results using the FM primer set to amplify DNA from four cucumber varieties in a PCR assay conducted according to the present invention.

Template DNA was isolated from each of the four cucumber species, as described in Example 1. The four cucumber varieties used were Chipper, Ashley, 42218, and 340625 (obtained from the USDA). The PCR assay was performed as described in Example 3, except that cucumber DNA was amplified using only the FM primer pair. FIG. 5 demonstrates the agarose gel results of this experiment. The gel in FIG. 5 was loaded as follows:

Lane 1: lambda DNA Marker; Lane 2: blank; Lane 3:
MR-1 Melon (resistant genotype) DNA amplified with the FM primers; Lane 4: AY Melon (susceptible genotype) DNA amplified with the AM primers; Lane 5: MR-1 Melon (resistant genotype) DNA amplified with the FM primers; Lane 6: AY Melon (susceptible genotype) DNA amplified with the AM primer set; Lane 7: blank; Lane 8: Chipper cucumber DNA amplified with the FM primer pair; Lane 9: Ashley cucumber DNA amplified with the FM primers; Lane 10: 422218 cucumber DNA amplified with the FM primers; Lane 11: 340625 cucumber DNA amplified with the FM primer pair; Lane 12: blank.

FIG. 5 shows that the FM primer set used in the PCR assay of the present invention successfully amplifies the expected PCR product when cucumber DNA was used as the template. A single band of the desired size was produced for all of the cucumber species tested. The results of this experiment indicate that the method of the present invention is useful for amplifying cucurbit DNA, in general, and melon DNA, specifically. In particular, the present invention is useful for identifying susceptible and resistant melon genotypes and provides an important tool for use in marker-assisted breeding programs.

Although preferred embodiments of the invention have been described using specific terms, devices, concentrations, and methods, such description is for illustrative purposes only. The words used are words of description rather of limitation. It is to be understood that changes in variations may be made with departing from the spirit of the scope of the following claims.

What is claimed is:

1. A method for objectively identifying a genotype resistant to Fusarium wilt disease in a whole cucurbit plant, plant extract, or plant seed by using cycles of a polymerase chain reaction, said method comprising the steps of:

(a) removing a sample of plant tissue from a cucurbit plant to be tested for a Fusarium-resistant genotype;

(b) extracting genomic DNA from said sample for use as a DNA template;

(c) replicating a desired region in the DNA template by binding a specific oligonucleotide primer set selected from the primer sets comprising Seq ID: 1 and Seq ID:2; and Seq. ID:3 and Seq ID:4 to said DNA template in a complimentary fashion, said primer set designed to give rise to a desired PCR product having a size different from the size of a product produced from amplifying undesired genomic DNA;

(d) amplifying complimentary DNA by conducting the polymerase chain reaction from about 30 cycles to about 40 cycles to produce a PCR product; and (e) examining said PCR product to determine if said product is amplified from a Fusarium-resistant cucurbit genotype.

2. The method in claim 1, wherein said cucurbit is a melon.

3. The method in claim 1, wherein said cucurbit is a cucumber.

4. The method in claim 1, wherein said Fusarium wilt disease is caused in cucurbits by *Fusarium oxysporum* infection.

5. The method as in claim 1, wherein said PCR product is examined by visualizing said PCR product in an ethidium bromide stained-agarose gel and comparing said PCR product to a standard DNA ladder to determine size of said PCR product.

6. The method as in claim 5, wherein the size of said desired PCR product is approximately 555 base pairs in length.

7. The method as in claim 5, wherein the size of said desired PCR product is approximately 1.682 kilobases in length.

8. The method in claim 1, wherein said PCR product is examined by colorimetric visualization, said method comprising the steps of:

(a) producing said PCR product containing a biotin moiety at a 5' end of a forward strand and a fluorescein moiety at a 5' end of a reverse strand of said PCR product;

(b) attaching said PCR product to a well of a microtiter plate, said well coated with avidin such that said PCR product is bound chemically via said biotin moiety, and subsequently washing away excess or unbound PCR product;

(c) attaching an enzyme to said PCR product via said fluorescein moiety, and subsequently washing away excess or unbound enzyme;

(d) adding a color substrate to said well, whereby said color substrate reacts with said enzyme to produce a colored product; and (e) measuring the intensity of said colored product using an ELISA reader.

9. The method as in claim 1, wherein said polymerase chain reaction is run for about 35 cycles.

10. A method for objectively identifying a genotype susceptible to Fusarium wilt disease in a whole cucurbit plant, plant extract, or plant seed by using cycles of a polymerase chain reaction, said method comprising the steps of:

(a) removing a sample of plant tissue from a cucurbit plant to be tested for a Fusarium-susceptible genotype;

(b) extracting genomic DNA from said sample for use as a DNA template;

(c) replicating a desired region in the DNA template by binding a specific oligonucleotide primer set selected from the primer sets comprising Seq ID:1 and Seq ID:2; and Seq. ID:3 and Seq ID:4 to said DNA template in a complimentary fashion, said primer set designed to give rise to a desired PCR product having a size different from the size of a product produced from amplifying undesired genomic DNA;

(d) amplifying complimentary DNA by conducting the polymerase chain reaction from about 30 cycles to about 40 cycles to produce a PCR product; and (e) examining said PCR product to determine if said product is amplified from a Fusarium-susceptible cucurbit genotype.

11. The method in claim 10, wherein said cucurbit is a melon.

12. The method in claim 10, wherein said cucurbit is a cucumber.

13. The method in claim 10, wherein said Fusarium wilt disease is caused in cucurbits by *Fusarium oxysporum* infection.

14. The method as in claim 10, wherein said PCR product is examined by visualizing said PCR product in an ethidium bromide stained-agarose gel and comparing said PCR product to a standard DNA ladder to determine size of said PCR product.

15. The method as in claim 14, wherein the size of said desired PCR product is approximately 596 base pairs.

16. The method as in claim 14, wherein the size of said desired PCR product is approximately 1.783 kilobases.

17. The method as in claim 10, wherein said PCR product is examined by colorimetric visualization, said method comprising the steps of:

(a) producing said PCR product containing a biotin moiety at a 5' end of a forward strand and a fluorescein moiety at a 5' end of a reverse strand of said PCR product;

(b) attaching said PCR product to a well of a microtiter plate, said well coated with avidin such that said PCR product is bound chemically via said biotin moiety, and subsequently washing away excess or unbound PCR product;

(c) attaching an enzyme to said PCR product via said fluorescein moiety, and subsequently washing away excess or unbound enzyme;

(d) adding a color substrate to said well, whereby said color substrate reacts with said enzyme to produce a colored product; and (e) measuring the intensity of said colored product using an ELISA reader.

18. The method as in claim 10, wherein said polymerase chain reaction is run for about 35 cycles.

* * * * *